US012636260B2

(12) United States Patent
Mao et al.

(10) Patent No.: US 12,636,260 B2
(45) Date of Patent: May 26, 2026

(54) APPLICATION OF α-ASARONE IN PREPARATION OF MEDICINE FOR PREVENTING OR TREATING HEMORRHAGIC STROKE

(71) Applicant: CHENGDU XINRUI TAIKANG TECHNOLOGY CO., LTD., Chengdu (CN)

(72) Inventors: Shengjun Mao, Chengdu (CN); Xiaofeng Gao, Chengdu (CN); Lijun Luo, Chengdu (CN); Rui Li, Chengdu (CN); Jian Zhang, Chengdu (CN); Peng Yang, Chengdu (CN); Di Zhang, Chengdu (CN); Qi Liu, Chengdu (CN); Huiyuan Yang, Chengdu (CN)

(73) Assignee: CHENGDU XINRUI TAIKANG TECHNOLOGY CO., LTD., Chengdu (CN)

( * ) Notice: Subject to any disclaimer, the term of this patent is extended or adjusted under 35 U.S.C. 154(b) by 548 days.

(21) Appl. No.: 18/029,362

(22) PCT Filed: Jul. 22, 2021

(86) PCT No.: PCT/CN2021/107800

§ 371 (c)(1),
(2) Date: Mar. 29, 2023

(87) PCT Pub. No.: WO2023/000247

PCT Pub. Date: Jan. 26, 2023

(65) Prior Publication Data

US 2023/0404945 A1 Dec. 21, 2023

(51) Int. Cl.
*A61K 31/09* (2006.01)
*A61K 9/107* (2006.01)
(Continued)

(52) U.S. Cl.
CPC .............. *A61K 31/09* (2013.01); *A61K 9/107* (2013.01); *A61K 47/44* (2013.01); *A61P 7/04* (2018.01); *A61P 25/08* (2018.01)

(58) Field of Classification Search
CPC ...... A61K 31/09; A61K 9/0019; A61K 9/107; A61P 7/04; A61P 25/08
See application file for complete search history.

(56) References Cited

FOREIGN PATENT DOCUMENTS

| | | | |
|---|---|---|---|
| CN | 101012159 | A | 8/2007 |
| CN | 102973499 | A | 3/2013 |

(Continued)

OTHER PUBLICATIONS

Ma et al., International Journal of Pharmaceutics 450 (2013) 21-30 (Year: 2013).*

(Continued)

*Primary Examiner* — San Ming R Hui

(57) ABSTRACT

The present invention provides an application of α-asarone in the preparation of a medicine for preventing or treating hemorrhagic strokes. α-asarone has the structure shown in formula I, and may significantly improve short-term neurological deficits and long-term learning and memory functions of model rats, reduce cerebral edema, improve the permeability of the blood-brain barrier, and prevent or mitigate the atrophy of brain tissue during a recovery period. α-asarone has a precise therapeutic effect on animal models of hemorrhagic stroke without obvious toxic side effects, and is expected to have great application prospects as a medicine for preventing/treating hemorrhagic strokes.

(Continued)

(I)

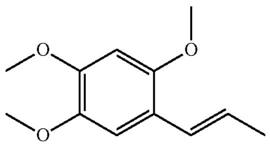

15 Claims, 6 Drawing Sheets

(51) Int. Cl.

| | |
|---|---|
| ***A61K 47/44*** | (2017.01) |
| ***A61P 7/04*** | (2006.01) |
| ***A61P 25/08*** | (2006.01) |

(56) References Cited

FOREIGN PATENT DOCUMENTS

| | | | |
|---|---|---|---|
| CN | 103655524 | A | 3/2014 |
| CN | 104587103 | A | 5/2015 |
| CN | 104940930 | A | 9/2015 |
| CN | 105943538 | A | 9/2016 |
| KR | 20000025941 | A | 5/2000 |
| KR | 20120138333 | A | 12/2012 |
| KR | 101355483 | B1 | 2/2014 |

OTHER PUBLICATIONS

Jun. 4, 2025 First Office Action Issued in Chinese Patent Application No. 202180089484.X.
May 16, 2025 First Search Report Issued in Chinese Patent Application No. 202180089484.X.
Mar. 11, 2025 Decision of Refusal Issued in Japanese Patent Application No. 2023-523130.
Toshiaki Takahashi et al., Mechanism of brain damage, The Japanese Society of Reanimatology, 2006, vol. 25, No. 1, pp. 1-11.
Nicole Pages et al., Activities of α-asarone in various animal seizure models and in biochemical assays might be essentially accounted for by antioxidant properties, Neuroscience research, 2010, 68(4): 337-344.
Gu, Quanbao et al., Effects of α-Asarone on the glutamate transporter EAAC1 in xenopus oocytes, Planta medica, 76.06 (2010): 595-598.
Shin, Jung-Won et al., α-Asarone ameliorates memory deficit in lipopolysaccharide-treated mice via suppression of pro-inflammatory cytokines and microglial activation, Biomolecules & therapeutics, 22.1 (2014): 17-26.
Takashi Moriya et al., Changes of extracellular glutamate concentration immediately after subarachnoid hemorrhage, Journal of the Japanese Society of Intensive Care Medicine, 11.2 (2004): 139-142.
Oct. 1, 2024 Notice of Reasons for Refusal issued in Japanese Patent Application No. 2023-523130.
Apr. 6, 2022 International Search Report issued in International Patent Application No. PCT/CN2021/107800.
Apr. 6, 2022 Written Opinion of the International Searching Authority issued in International Patent Application No. PCT/CN2021/107800.
Jul. 19, 2021 International Search Report issued in International Patent Application No. PCT/CN2021/095672.
Jul. 19, 2021 Written Opinion of the International Searching Authority issued in International Patent Application No. PCT/CN2021/095672.
Chao Zhou et al., Clinical Observation on Prevention and Treatment of Delayed Cerebral Vasospasm after Subarachnoid Hemorrhage by Combination of Traditional Chinese and Western Medicine, Journal of New Chinese Medicine, vol. 44, No. 11, Nov. 5, 2012, ISSN: 0256-7415, Abstract, Section 2.2 and Section 5.
Jianjia Chen, Observation on Curative Effect of α-asarone in Rescuing Status Epilepticus in 18 Cases, Journal of Traditional Chinese Medicine, No. 12, Dec. 27, 1982, ISSN: 1001-1668, Text, Paragraphs 1-5, and Section 4.
Jiufu Gu et al., Clinical Progress on the Xinnao Kaiqiao Preparations and its Application in Cerebral Hemorrhage Coma, Clinical Journal of Traditional Chinese Medicine, vol. 29, No. 1, Feb. 14, 2017, ISSN: 1672-7134, Paragraph 1, Section 2 and p. 137, Left Column, Paragraph 5.
Feifei Xu et al., Research Progress on the Neuropharmacological Effects and Mechanisms about the Main Components α- and β-Asarone in Volatile Oils of Acorus Tatarrinowii Schott, Natural Product Research and Development, vol. 32, No. 11, Jul. 29, 2020, ISSN: 1001-6880, Entire Document.
Hong Ju Lee et al., Positive Effects of α-asarone on Transplanted Neural Progenitor Cells in a Murine Model of Ischemic Stroke, Phytomedicine, vol. 51, Dec. 31, 2018, pp. 151-161.
Zhouquan Cai et al., Preparation and Quality Evaluation of α-asarone Intravenous Emulsion, West China Journal of Pharmaceutical Sciences, vol. 22, No. 6, Dec. 31, 2007, pp. 611-613.
Young Ock Kim et al., Effects of α-asarone against Global Cerebral Ischemia in Rats, Natural Product Sciences, vol. 15, No. 4, Dec. 31, 2009, pp. 198-202.
Wang Z J et al., Identification of both GABAA receptors and voltage-activated Na+ channels as molecular targets of anticonvulsant alpha-asarone, [J]. Front Pharmacol, 2014, 5 (40): 5-11.
Huang C et al., Alpha-asarone from Acorus gramineus alleviates epilepsy by modulating A-type GABA receptors, [J]. Neuropharmacology, 2013, 65 (2): 1-11.
Chellian R et al., Pharmacology and Toxicology of α- and β-Asarone: A Review of Preclinical Evidence, [J]. Phytomedicine, 2017: 41-58.
Chinese Society of Neurology, Chinese Stroke Society, Chinese guidelines for diagnosis and treatment of acute intracerebral hemorrhage 2019, Chinese Journal of Neurology, Dec. 2019, vol. 52, No. 12, 994-1005.
George Paxinos et al., The Rat Brain in Stereotaxic Coordinates, People's Medical Publishing, 2005, Third Edition, Fig. 17-19.
Apr. 5, 2024 Extended European Search Report issued in European Patent Application No. 21950502.1.

* cited by examiner

APPLICATION OF α-ASARONE IN PREPARATION OF MEDICINE FOR PREVENTING OR TREATING HEMORRHAGIC STROKE

The present application is a National Stage of International Application No. PCT/CN2021/107800, filed on Jul. 22, 2021.

TECHNICAL FIELD

The present disclosure belongs to the biomedical field and relates to the use of α-asarone in the manufacture of a medicament for preventing or treating hemorrhagic stroke.

BACKGROUND

Stroke is now the second leading cause of death in the world. Only in China, there are nearly 4 million new cases every year with the highest incidence rate worldwide. There are more than 2 million deaths due to stroke every year, and about ⅔ of stroke survivors are permanently disabled. Stroke can be clinically divided into ischemic stroke and hemorrhagic stroke. Hemorrhagic stroke refers to a series of clinical manifestations, such as neurological dysfunctions caused by the rupture of intracranial blood vessels and the leakage of blood into the brain. Although the incidence of hemorrhagic stroke is relatively low, it has high rates of mortality and disability. Depending on the bleeding site in the brain, hemorrhagic stroke is mainly divided into two types: intracerebral hemorrhage (ICH) and subarachnoid hemorrhage (SAH). ICH occurs in the brain, while SAH occurs between the pia mater and the arachnoid. Hypertensive cerebral hemorrhage is the most common cause of non-traumatic ICH, while common causes of SAH are intracranial aneurysms.

Brain injury caused by hemorrhagic stroke is difficult to treat in the clinic and is an important cause of disability. Brain injury can be divided into two types: primary and secondary brain injury. The primary brain injury refers to direct mechanical compression injury and consequent ischemic changes of surrounding brain tissue caused by hematoma and its enlargement formed by initial hemorrhage, including excessive glutamate release, calcium overload, mitochondrial dysfunction, etc. However, the mechanism of secondary brain injury is relatively complex, and its pathological pathways include disruption of the blood-brain barrier and formation of brain edema, oxidative stress and inflammatory response, autophagy and apoptosis, microglia activation, energy metabolism and proteomic alternations in the brain, iron deposition, etc., finally leading to neurological deficits. The pathological mechanism of brain injury induced by hemorrhagic stroke involves multiple factors and links, of which interrelated and interacted with each other. Among them, the neuronal excitotoxicity caused by the imbalance in the regulation excitatory amino acids (such as glutamate) and inhibitory amino acids (such as γ-aminobutyric acid, GABA) is a key factor leading to the neuronal injury and death in the acute phase of hemorrhagic stroke.

Currently, patients with hemorrhagic stroke are mainly treated with drug remedies and surgical procedures in the clinic. Drug remedies are mainly medical symptomatic treatments, including intracranial pressure reduction, blood pressure adjustment, hemostatic treatment, mild hypothermia treatment, brain metabolic activator, calcium antagonist, etc., but with poor efficacy. Surgical treatment indeed plays a positive role in saving patients' lives, but has no satisfactory curative effect on patients' neurological dysfunctions, and has relatively strict applicable requirements. To date, no drug treatment has been approved for the rescue of neurological damage caused by hemorrhagic stroke, thereby increasing patient survival or improving patient prognosis. Therefore, it is of great clinical significance to develop drugs that can effectively treat hemorrhagic stroke.

α-Asarone (alpha-asarone) is the main active ingredient of traditional Chinese medicine *Acorus tatarinowii*, with sedative, antispasmodic, anticonvulsant, and other effects. Studies have shown that α-asarone can exert antiepileptic effects by blocking $Na^+$ channels and activating $GABA_A$ receptors (see Wang Z J, Levinson S R, Sun L, et al. Identification of both $GABA_A$ receptors and voltage-activated $Na^+$ channels as molecular targets of anticonvulsant alpha-asarone [J]. Front Pharmacol, 2014, 5(40):5-11 and Huang C, Li W G, Zhang X B, et al. alpha-asarone from Acorus gramineus alleviates epilepsy by modulating A-type GABA receptors [J]. Neuropharmacology, 2013, 65(2):1-11). In addition, it can also promote the proliferation of neural progenitor cells and reduce oxidative stress, microglia activation, neuroinflammation, and neuronal apoptosis (see Chellian R, Pandy V, Mohamed Z. Pharmacology and toxicology of α- and β-Asarone: A review of preclinical evidence [J]. Phytomedicine, 2017:41-58). Although the above studies suggest that α-asarone has a variety of neuropharmacological activities, the therapeutic effect of α-asarone on hemorrhagic stroke has not been reported so far.

On the other hand, in the clinical treatment of secondary epilepsy caused by hemorrhagic stroke, prophylactic administration of antiepileptic drug is generally not recommended (Neurology Branch of Chinese Medical Association, Cerebrovascular Disease Group of Neurology Branch of Chinese Medical Association, Guidelines for Diagnosis and Treatment of Brain Hemorrhage in China 2019 [J]. Chinese Journal of Neurology, 2019, 52 (12):994-1005.). The reason is that antiepileptic drugs have strong side effects, and prophylactic administration of antiepileptic drugs may damage the neurological function of patients with hemorrhagic stroke.

CONTENT OF THE PRESENT INVENTION

In order to overcome the problem in the prior art of lack of medicaments for preventing or treating hemorrhagic stroke, the present disclosure provides new use of α-asarone.

To this end, the present disclosure provides the following technical solutions:

The present disclosure provides the use of a compound represented by formula I (trans-2,4,5-trimethoxy-1-propenylbenzene, also known as α-asarone, α-asaron) in the manufacture of a medicament for preventing or treating hemorrhagic stroke;

(I)

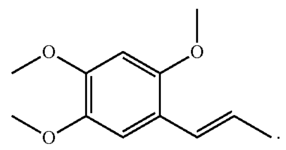

The present disclosure surprisingly finds that the compound represented by formula I can significantly ameliorate the short-term neurological impairment and long-term learning and memory function of model rats, reduce brain edema, improve the permeability of blood-brain barrier, and prevent or relieve the atrophy of brain tissue during recovery phases. The compound has an accurate therapeutic effect on animal models of hemorrhagic stroke, and does not show obvious toxic and side effects. In the present disclosure, α-asarone, the positive drug vinpocetine injection and nimodipine injection are used to treat subarachnoid hemorrhagic rats established by endovascular perforation and intracerebral hemorrhagic rats established by collagenase injection. It is found that α-asarone can significantly relieve the brain edema of the ipsilateral brain tissue in model rats, improve the permeability of the blood-brain barrier, prevent or alleviate the brain tissue atrophy of model rats in a recovery phase, thereby significantly improving the short-term neurological function score and long-term learning and memory function. At the same time, α-asarone can also significantly reduce the mortality and the incidence of secondary epilepsy in model rats with acute hemorrhagic stroke and prolong their survival.

In some embodiments, the medicament is also used for preventing or treating secondary epilepsy caused by hemorrhagic stroke. Preferably, the medicament is used for treating hemorrhagic stroke and preventing secondary epilepsy caused by hemorrhagic stroke.

In some embodiments, the hemorrhagic stroke is a stroke caused by at least one of intracerebral hemorrhage (ICH) and subarachnoid hemorrhage (SAH).

In the present disclosure, the compound represented by formula I can have the following pharmacological effects: (1) antagonizing neuronal excitotoxicity caused by excessive glutamate; (2) reducing abnormally elevated glutamate and GABA levels; (3) inhibiting neuronal calcium influx and intracellular calcium overload; (4) stabilizing the neurons' mitochondrial membrane potential and reducing neuronal apoptosis; (5) relieving oxidative stress responses of damaged neurons.

In the present disclosure, the medicament can have the following pharmacological effects: (1) antagonizing neuronal excitotoxicity caused by excessive glutamate; (2) reducing abnormally elevated glutamate and GABA levels; (3) inhibiting neuronal calcium influx and intracellular calcium overload; (4) stabilizing the neurons' mitochondrial membrane potential and reducing neuronal apoptosis; (5) relieving oxidative stress responses of damaged neurons.

In the present disclosure, the medicament can (1) reduce the glutamate content in the brain of a model rat, thereby antagonizing the glutamate excitotoxicity caused by cerebral hemorrhage; (2) restore GABA levels, and promote the recovery of motor functions for model rats; (3) reduce $Ca^{2+}$ influx, and alleviate adverse biochemical reactions and excitotoxicity caused by $Ca^{2+}$ overload; (4) stabilize mitochondrial membrane potential and reduce neuronal apoptosis; (5) reduce neuronal oxidative stress and injury, thus reducing brain edema, improving the permeability of blood-brain barrier, preventing or alleviating brain tissue atrophy during recovery phases, ameliorating short-term neurological impairment and long-term learning and memory dysfunction in model rats, and exerting an anti-hemorrhagic stroke effect.

In some embodiments, the medicament is used for at least one of the following: ameliorating neurological or motor dysfunction (such as neurological or motor dysfunction caused by ICH or SAH), alleviating secondary early brain injury (such as brain edema or blood-brain barrier dysfunction in acute phase, such as brain edema or blood-brain barrier dysfunction in acute phase caused by ICH or SAH), reducing the mortality in acute phase caused by hemorrhagic stroke, prolonging survival, ameliorating long-term learning and memory dysfunction caused by hemorrhagic stroke, and preventing or alleviating brain tissue atrophy during recovery phase from hemorrhagic stroke.

In some embodiments, the compound represented by formula I is the only active ingredient in the medicament.

In some embodiments, the medicament can comprise pharmaceutical excipients. Preferably, the total weight ratio of the compound represented by formula I to the pharmaceutical excipient is 1:20 to 1000, for example, 1:20 to 200. More preferably, the compound represented by formula I is the only active ingredient in the medicament, and the total weight ratio of the compound represented by formula I to the pharmaceutical excipient is 1:20 to 1000, for example, 1:20 to 200.

In some embodiments, the subject to whom the medicament is administrated can be a human or an animal. When the medicament is used for treating model rats with hemorrhagic stroke, the daily effective dosage of the compound represented by formula I in the medicament can be 5 mg to 40 mg/kg body weight. When the medicament is used for treating a human suffering from hemorrhagic stroke, the daily administration dosage range of the compound represented by formula I in the medicament can be 0.15 mg to 5.0 mg/kg body weight, preferably 0.3 mg to 3.0 mg/kg body weight, for example, the medicament is administrated 2 to 3 times a day with a dosage range from 0.15 mg to 1.5 mg/kg body weight, preferably 0.3 mg to 1.5 mg/kg body weight. The above dosages can be obtained according to the dosage conversion relationship between different species of animals.

In some embodiments, the administration route of the medicament is injection administration, oral administration, subcutaneous implantation administration, inhalation administration, transdermal administration, mucosal administration, etc. Preferably, the administration route of the medicament is injection administration (preferably intravenous administration) or oral administration.

In the present disclosure, the medicament can be made in a dosage form suitable for human and/or animal use, such as any dosage form compatible with different administration routes, provided that the dosage form allows the compound represented by formula I to enter the brain and reach an effective therapeutic concentration. In some embodiments, the medicament is an emulsion (e.g., emulsion injection, oral emulsion). The emulsion has a better safety profile than current commercial injection and a higher bioavailability than tablets.

In some embodiments, the emulsion can comprise the compound represented by formula I, a pharmaceutically acceptable oil, a pharmaceutically acceptable emulsifier and water.

Among them, the pharmaceutically acceptable oil can be composed of at least one of soybean oil, medium chain oil, olive oil and fish oil.

Among them, the pharmaceutically acceptable emulsifier can be composed of at least one of egg yolk lecithin, soybean lecithin, Pluronic F-68 and polyoxyl 15 hydroxystearate (Solutol HS15).

Among them, the water can be water for injection or purified water.

Among them, according to the requirement of emulsifying performance, the emulsion can also comprise at least one of oleic acid and sodium oleate. During preparation, oleic acid is dissolved in oil phase, sodium oleate is dissolved in aqueous phase, and the mixture of them can be dissolved in oil and aqueous phases respectively.

Among them, the emulsion can also comprise glycerol.

Among them, the emulsion can also comprise an antioxidant. The antioxidant can be sodium bisulfite, vitamin E, pyrogallic acid ester, etc.

Among them, when administrated orally, the emulsion can also comprise at least one of other suitable additives such as preservatives and flavoring agents. The preservative can be a conventional preservative in the art, such as benzoic acid, sodium benzoate, sorbic acid, potassium sorbate, ethyl, propyl, and butylparaben. The flavoring agent can be a conventional flavoring agent in the art, such as a sweetener, a fragrance, a hydrogel or an effervescing agent. Among them, the sweetener can be simple syrup, stevioside, aspartame, etc.; among them, the fragrance can be fruit fragrance, such as apple fragrance and strawberry fragrance; among them, the hydrogel can be gelatin, methyl cellulose, etc.; among them, the effervescing agent can be a mixture of citric acid, tartaric acid and sodium bicarbonate.

In some embodiments, the emulsion can comprise 0.5% to 5% by weight of the compound represented by formula I, 5% to 30% by weight of the pharmaceutically acceptable oil, 0.6% to 1.8% by weight of the emulsifier, 0% to 2.5% by weight of the glycerol, and a residual amount of water (e.g., purified water or water for injection). The concentration of the compound represented by formula I in the emulsion can vary within a certain range, and the range of the concentration varies depending on the amount and volume to be administrated, and the solubility of the compound represented by formula I in the oil phase.

In some embodiments, the emulsion is emulsion injection. Preferably, in the emulsion injection, the total weight ratio of the compound represented by formula I to the pharmaceutical excipient (comprising water for injection) is 1:20 to 1000, for example, 1:20 to 200.

Among them, the preparation method of the emulsion can comprise the following steps: mixing the compound represented by formula I, the pharmaceutically acceptable oil, the pharmaceutically acceptable emulsifier and water by high-speed shearing to obtain a primary emulsion; homogenizing the primary emulsion under high pressure to obtain the emulsion.

In some embodiments, the preparation method of the emulsion can comprise the following steps:

step 1: under the protection of nitrogen or an inert gas, dissolving the compound represented by formula I in the pharmaceutically acceptable oil at 60 to 80° C. to obtain an oil phase, and then dissolving or dispersing the emulsifier and glycerol in water at 60 to 80° C. to obtain an aqueous phase; or, under the protection of nitrogen or an inert gas, dissolving or dispersing the compound represented by formula I and the emulsifier in the pharmaceutically acceptable oil at 60 to 80° C. to obtain an oil phase, and then dissolving glycerol in water at 60 to 80° C. to obtain an aqueous phase;

step 2, mixing the oil phase and the aqueous phase by high-speed shearing, and dispersing the oil phase in the aqueous phase to obtain a primary emulsion;

step 3: homogenizing the primary emulsion under high pressure (the number of times for homogenization under high pressure can be 1 to 3 times), so that the average particle size of the emulsion droplet is not greater than 0.5 μm, filtering, and filling into pharmaceutical containers such as a glass ampoule, an infusion bottle, a penicillin bottle, and a soft bag under the protection of nitrogen or an inert gas; according to the need of the administration route, emulsions are obtained by rotary hot pressing sterilization or adding preservatives without sterilization.

The shear rate of the high-speed shearing can be a conventional shear rate used in the preparation of emulsions in small-scale trial production or large-scale production in the art. For example, the shear rate of the laboratory small-scale trial production can be 10000 to 20000 $r \cdot min^{-1}$, and the shear rate of the large-scale production is 2000 to 4000 $r \cdot min^{-1}$. The actual shear rate depends on the shear radius, both of which determine the magnitude of the shear force.

The shear time of the high-speed shearing can be a conventional shear time used in the preparation of emulsions in the art, for example, it can be 3 to 10 minutes, for another example, 5 to 8 minutes.

The homogenizing pressure of the high-pressure homogenization can be a conventional homogenizing pressure used in the preparation of emulsions in the art, for example, it can be 500 to 1500 bar, for another example, 500 to 1000 bar.

The number of cycles of the high-pressure homogenization can be a conventional number of cycles used in the preparation of emulsions in the art, for example, it can be 1 to 3 times.

The present disclosure also provides a pharmaceutical composition for preventing or treating hemorrhagic stroke, wherein the pharmaceutical composition comprises the compound represented by formula I and pharmaceutical excipients.

In some embodiments, the pharmaceutical composition is also used for preventing or treating secondary epilepsy caused by hemorrhagic stroke.

In some embodiments, the pharmaceutical composition is used for treating hemorrhagic stroke and preventing secondary epilepsy caused by hemorrhagic stroke.

In some embodiments, the compound represented by formula I is the only active ingredient in the pharmaceutical composition.

In some embodiments, the pharmaceutical composition is an emulsion.

The present disclosure also provides a method for treating or preventing hemorrhagic stroke in a subject, comprising: administrating a therapeutically or prophylactically effective amount of the compound represented by formula I to the subject.

Preferably, the method is used to treat or prevent a hemorrhagic stroke in a subject and to treat or prevent secondary epilepsy caused by hemorrhagic stroke.

More preferably, the method is used to treat hemorrhagic stroke in a subject and to prevent secondary epilepsy caused by hemorrhagic stroke.

DEFINITION AND DESCRIPTION

Unless otherwise stated, the following terms and phrases used herein are intended to have the following meanings. A specific term or phrase should not be regarded as uncertain or unclear without special definition, but should be understood according to its ordinary meaning. When a trade name appears herein, it is intended to refer to its corresponding commodity or its active ingredients.

Unless otherwise stated, in the present disclosure, the term "pharmaceutically acceptable" refers to those compounds, materials, compositions and/or dosage forms, which are within the scope of reliable medical judgment and are suitable for contact with human and animal tissues without excessive toxicity, irritation, allergic reaction or other problems or complications, and are commensurate with a reasonable benefit/risk ratio.

Unless otherwise stated, in the present disclosure, the term "pharmaceutically acceptable amount" refers to the amount of those compounds, materials, compositions and/or dosage forms, which are within the range of reliable medical judgment without excessive toxicity, irritation, allergic reaction or other problems or complications, and are commensurate with a reasonable benefit/risk ratio.

Unless otherwise stated, the term "pharmaceutical excipients" refers to the vehicle and additives used in the production of medicaments and the preparation of prescriptions, and refers to all substances contained in pharmaceutical preparations except active ingredients. See the Pharmacopoeia of the People's Republic of China (2020 Edition), Part IV, or Handbook of Pharmaceutical Excipients (Raymond C Rowe, 2009 Sixth Edition).

Unless otherwise stated, the term "treatment" refers to therapeutic therapy. When referring to a specific condition, treatment means (1) alleviating one or more biological manifestations of the disease or condition, (2) interfering with (a) one or more points in the biological cascade causing or contributing to the condition or (b) one or more biological manifestations of the condition, (3) improving one or more symptoms, effects, or side effects related to the condition, or improving one or more symptoms, effects or side effects related to the condition or its treatment, or (4) slowing the development of the condition or one or more biological manifestations of the condition.

Unless otherwise stated, the term "prevention" means a reduction in the risk of acquiring or developing a disease, disorder or condition.

Unless otherwise stated, the term "therapeutically effective amount" refers to an amount of a compound that is sufficient to effectively treat the diseases or conditions described herein when administrating to a subject. The "therapeutically effective amount" will vary according to the compound, the condition and its severity, and the age of the patient to be treated, but can be adjusted by those skilled in the art as needed. The effective amount varies with different subjects of administration (such as human or animal).

Unless otherwise stated, the term "prophylactically effective amount" refers to an amount sufficient to prevent diseases, disorders or conditions, or an amount sufficient to prevent one or more symptoms related to diseases, disorders or conditions, or an amount to prevent recurrence of diseases, disorders or conditions.

Unless otherwise stated, the term "subject" refers to any animal, preferably mammal, most preferably human, that is about to receive or has received administration of the compound according to embodiments of the present disclosure. The term "mammal" includes any mammal. Examples of mammals include, but are not limited to, cattle, horses, sheep, pigs, cats, dogs, mice, rats, rabbits, guinea pigs, monkeys, humans, etc., most preferably humans.

Where the reaction temperature is not specified in the present disclosure, the reaction temperature is room temperature, and the room temperature is generally 20 to 35° C.

Unless otherwise stated, "secondary epilepsy caused by hemorrhagic stroke" in the present disclosure refers to secondary epileptic seizures (excluding lesions unrelated to the hemorrhagic stroke) caused by hemorrhagic stroke in a patient who has no history of epilepsy.

On the basis of not violating the common knowledge in the art, the above preferred conditions can be arbitrarily combined to obtain the preferred examples of the present disclosure.

The reagents and raw materials used in the present disclosure are commercially available.

The positive progressive effect of the present disclosure is that:

The present disclosure discloses for the first time that α-asarone has the effect of treating/preventing hemorrhagic stroke, and the research results of pharmacodynamic mechanism show that α-asarone can (1) reduce glutamate content in a model rat, thereby antagonizing the glutamate-involved excitotoxicity caused by cerebral hemorrhage; (2) restore GABA levels, and promote the recovery of motor functions in model rats; (3) reduce $Ca^{2+}$ influx, and alleviate adverse biochemical reactions and excitotoxicity caused by $Ca^{2+}$ overload; (4) stabilize mitochondrial membrane potential and reduce neuronal apoptosis; (5) reduce neuronal oxidative stress and injury, thus reducing brain edema, attenuating brain injury, improving the permeability of blood-brain barrier, preventing or alleviating brain tissue atrophy during recovery phases, thus alleviating short-term neurological impairment and long-term learning and memory dysfunction in model rats, significantly reducing the mortality and the incidence of secondary epilepsy of model rats in the acute phase, prolonging their survival time, increasing their survival rate, and improving their prognosis, thereby exerting an anti-hemorrhagic stroke effect.

The present disclosure surprisingly finds that α-asarone has a significantly better effect than vinpocetin injection on alleviating neurological impairment of model rats in the acute phase of SAH, and it is more effective than nimodipine injection in improving learning and memory function and preventing or alleviating brain atrophy of model rats in the recovery phase of SAH. Moreover, it exerts better effect than nimodipine and vinpocitine injection on alleviating the neurological deficits of ICH rats. Accordingly, α-asarone is expected to be a prophylactic/therapeutic medicament in the hemorrhagic stroke with extreme prospect of application.

α-Asarone is safe and effective, with no obvious toxic and side effects observed during all the experiments of the present disclosure.

BRIEF DESCRIPTION OF THE DRAWINGS

FIG. 1A. The escape latency for rats in each group during the training period. FIG. 1B. The dwelling time in the target quadrant and swimming speed for rats in each group during the probe test. FIG. 1C. The track heatmaps for rats in each group in the probe test and the circle indicates the platform position and its quadrant is the target quadrant. FIG. 1D. The brain atrophy of rats in each group after completing the water maze test and obtaining the rat's brain by transcardinal perfusion. P, S, M and N respectively represent sham, SAH, medium-dose α-asarone, and nimodipine injection groups. ###P<0.001, ##p<0.01, #P<0.05 vs. sham group, ** P<0.01, *P<0.05 vs. the model group, and &&&P<0.001, &&P<0.01 vs. medium-dose α-asarone group.

FIG. 2A. Water content in different parts of brain tissue for SAH rats in each group. FIG. 2B. Evans blue extravasation in brain tissue of SAH rats in each group. FIG. 2C. Water content in different parts of brain tissue for ICH rats in each group. FIG. 2D. Evans blue extravasation in brain tissue of ICH rats in each group. P, S, I, M represent sham, SAH, ICH, and medium-dose α-asarone groups, respectively. ###p<0.001, ##p<0.01, #P<0.05 vs. sham group, P<0.05 vs. the model group.

FIG. 3A. Glutamate content in brain tissue of SAH rats in each group. FIG. 3B. GABA content in brain tissue of SAH rats in each group. FIG. 3C. Glutamate content in brain tissue around hematoma of ICH rats in each group. FIG. 3D. GABA content in brain tissue around hematoma of ICH rats in each group. ##P<0.01, P<0.05 vs. sham group, *P<0.05 vs. the model group.

FIG. 4A. The curves of calcium level in brain tissue of SAH rats in each group. FIG. 4B. The curves of mitochondrial membrane potential in brain tissue of SAH rats in each group. FIG. 4C. The statistical analyses of mean fluorescence intensity for calcium ion and mitochondrial membrane potential in brain tissue of SAH rats in each group. FIG. 4D. The curves of calcium level in brain tissue of ICH rats in each group. FIG. 4E. The curves of mitochondrial membrane potential in brain tissue of ICH rats in each group. FIG. 4F. The statistical analyses of mean fluorescence intensity for calcium ion and mitochondrial membrane potential in brain tissue of ICH rats in each group. ###P<0.001, ##p<0.01, #P<0.05 vs. sham group, *** P<0.001, P<0.05 vs. the model group.

DETAILED DESCRIPTION OF THE PREFERRED EMBODIMENT

Figure 1A:
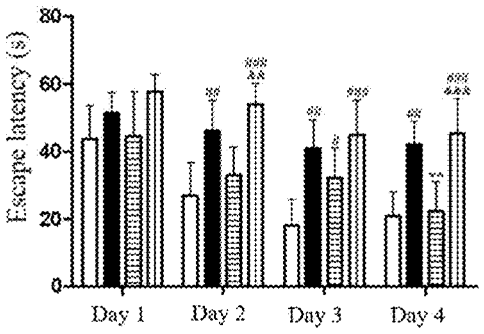
FIGS. 1A-1D. Effects of α-asarone on the learning and memory function and brain tissue atrophy of SAH rats in recovery phase.

The present disclosure is further described below by way of embodiments, but the present disclosure is not thereby limited to the scope of the described embodiments. The experimental methods for which specific conditions are not indicated in the following embodiments are selected according to conventional methods and conditions, or according to the commercial specification.

Preparation Embodiment 1 Preparation of α-Asarone Injection Emulsion 0.50 to 50.0 g of α-asarone and 50.0 to 300.0 g of soybean oil for injection were weighed, placed in a suitable container, heated to 60 to 80° C. under the protection of nitrogen, and stirred to dissolve; 6.0 to 18.0 g of egg yolk lecithin was then weighed, and added thereto, and the mixture was stirred to dissolve (if necessary, 0.10 to 0.50 g of oleic acid, sodium oleate or their mixture was added) to prepare an oil phase for use. Also 0 to 3.0 g of Pluronic (F68) and 0 to 25.0 g of glycerol were weighed, and added to about 800 mL of water, and the mixture was heated to 60 to 80° C. under the protection of nitrogen, stirred to dissolve to prepare an aqueous phase. The above oil phase was added to the aqueous phase, and the mixture was sheared at high speed for 5 to 15 minutes, and additional water was added to a total volume of 1000 mL to prepare a primary emulsion. The primary emulsion was then homogenized 1 to 3 times by high-pressure homogenizer, so that the average particle size of the homogenized emulsion droplets was not more than 0.5 μm, filtered with a filter membrane, and the filtrate was filled in 5 mL to 20 mL glass ampoule under the protection of nitrogen, sterilized by rotary hot pressing at 121° C. for 8 to 12 min to obtain α-asarone injection emulsion, wherein the concentration of α-asarone was 0.5 to 50 mg/mL.

Preparation Embodiment 2 Preparation of α-Asarone Injection Emulsion 10.0 g of α-asarone, 50.0 g of soybean oil for injection and 50.0 g of medium chain triglyceride (MCT) for injection were weighed, placed in a suitable container, heated to 60 to 80° C. under the protection of nitrogen, and stirred to dissolve; 12.0 g of egg yolk lecithin and 0.3 g of sodium oleate were then weighed, and added thereto, and the mixture was stirred to dissolve to prepare an oil phase for use. Also 22.0 g of glycerol was weighed, and added to about 800 mL of water, and the mixture was heated to 60 to 80° C. under the protection of nitrogen, stirred to dissolve to prepare an aqueous phase. The above oil phase was added to the aqueous phase, and the mixture was sheared at high speed for 5 to 15 minutes, and additional water was added to a total volume of 1000 mL to prepare a primary emulsion. The primary emulsion was then homogenized 1 to 3 times by high-pressure homogenizer, so that the average particle size of the homogenized emulsion droplets was not more than 0.5 μm, filtered with a filter membrane, and the filtrate was filled in 5 mL or 10 mL glass ampoule under the protection of nitrogen, sterilized by rotary hot pressing at 121° C. for 8 min to obtain α-asarone injection emulsion, wherein the concentration of α-asarone was 10 mg/mL.

Preparation Embodiment 3 Preparation of α-Asarone Injection Emulsion 20.0 g of α-asarone, 100.0 g of soybean oil for injection and 100.0 g of medium chain triglyceride (MCT) for injection were weighed, placed in a suitable container, heated to 60 to 80° C. under the protection of nitrogen, and stirred to dissolve; 12.0 g of egg yolk lecithin and 0.3 g of oleic acid were then weighed, and added thereto, and the mixture was stirred to dissolve to prepare an oil phase for use. Also 22.0 g of glycerol was weighed, and added to about 800 mL of water, and the mixture was heated to 60 to 80° C. under the protection of nitrogen, stirred to dissolve to prepare an aqueous phase. The above oil phase was added to the aqueous phase, and the mixture was sheared at high speed for 5 to 15 minutes, and additional water was added to a total volume of 1000 mL to prepare a primary emulsion. The primary emulsion was then homogenized 1 to 3 times by high-pressure homogenizer, so that the average particle size of the homogenized emulsion droplets was not more than 0.5 μm, filtered with a filter membrane, and the filtrate was filled in 5 mL or 10 mL glass ampoule under the protection of nitrogen, sterilized by rotary hot pressing at 121° C. for 8 min to obtain α-asarone injection emulsion, wherein the concentration of α-asarone was 20 mg/mL.

Preparation Embodiment 4 Preparation of α-Asarone Injection Emulsion 1.0 g of α-asarone and 100.0 g of soybean oil for injection were weighed, placed in a suitable container, heated to 60 to 80° C. under the protection of nitrogen, and stirred to dissolve; 12.0 g of egg yolk lecithin and 0.3 g of oleic acid were then weighed, and added thereto, and the mixture was stirred to dissolve to prepare an oil phase for use. Also 22.0 g of glycerol was weighed, and added to about 800 mL of water, and the mixture was heated to 60 to 80° C. under the protection of nitrogen, stirred to dissolve to prepare an aqueous phase. The above oil phase was added to the aqueous phase, and the mixture was sheared at high speed for 5 to 15 minutes, and additional water was added to a total volume of 1000 mL to prepare a primary emulsion. The primary emulsion was then homogenized 1 to 3 times by high-pressure homogenizer, so that the average particle size of the homogenized emulsion droplets was not more than 0.5 μm, filtered with a filter membrane, and the filtrate was filled in 50 mL infusion bottle under the protection of nitrogen, sterilized by rotary hot pressing at 121° C. for 12 min to obtain α-asarone injection emulsion, wherein the concentration of α-asarone was 1 mg/mL.

Preparation Embodiment 5 Preparation of α-Asarone Oral Emulsion

The preparation method was the same as embodiment 1, a pharmaceutically acceptable amount of antioxidant (such as vitamin E, pyrogallic acid ester) was added to the oil phase; and a pharmaceutically acceptable amount of preservative (such as ethylnipagin) could also be added to the oil phase; and a pharmaceutically acceptable amount of flavoring agent (such as fruit juice syrup with aromatic flavor) could be added to the aqueous phase; a pharmaceutically acceptable amount of preservative (such as benzoic acid, sodium benzoate) could also be added to the aqueous phase. The primary emulsion was prepared by the same method, and the primary emulsion was then homogenized 1 to 3 times by high-pressure homogenizer, so that the average particle size of the homogenized emulsion droplets was not more than 10 μm, filtered with a filter membrane, and the filtrate was filled in a suitable medicinal package under the protection of nitrogen, sterilized by circulating steam at 100° C. for 30 min or at 121° C. for 8 min to obtain α-asarone oral emulsion.

Preparation Embodiment 6 Preparation of α-Asarone Injection Emulsion 1.0 g to 20.0 g of α-asarone and 50.0 g to 200.0 g of soybean oil for injection were weighed, placed in a suitable container, heated to 60 to 80° C. under the protection of nitrogen, and stirred to dissolve; 12.0 g of egg yolk lecithin and 0 to 0.3 g of oleic acid were then weighed, and added thereto, and the mixture was stirred to dissolve to prepare an oil phase for use. Also 22.0 g of glycerol was weighed, and added to about 800 mL of water, and the mixture was heated to 60 to 80° C. under the protection of nitrogen, stirred to dissolve to prepare an aqueous phase. The above oil phase was added to the aqueous phase, and the mixture was sheared at high speed for 5 to 15 minutes, and additional water was added to a total volume of 1000 mL to prepare a primary emulsion. The primary emulsion was then homogenized 1 to 3 times by high-pressure homogenizer, so that the average particle size of the homogenized emulsion droplets was not more than 0.5 μm, filtered with a filter membrane, and the filtrate was filled in 2 mL, 5 mL, 10 mL glass ampoules under the protection of nitrogen, sterilized by rotary hot pressing at 121° C. for 8 to 12 min to obtain α-asarone emulsion injection, wherein the content of α-asarone was 1 mg/mL to 20 mg/mL.

Preparation Embodiment 7 Preparation of α-Asarone Injection Emulsion (Also Known as Emulsion Injection)

Experimental Materials:

α-Asarone (2883-98-9, Wuhan Lullaby Pharmaceutical Chemical Co., Ltd.);

soybean oil for injection (DD20200603, Shandong Ruisheng Pharmaceutical Excipients Co., Ltd.);

egg yolk lecithin (202008013, Shanghai Tywei Pharmaceutical Co., Ltd.);

oleic acid (160907, Xi'an Libang Pharmaceutical Co., Ltd.);

glycerol (20191213, Zhejiang Suichang Huikang Pharmaceutical Co., Ltd.);

experimental steps: 10.0 g of α-asarone and 100.0 g of soybean oil for injection were weighed, placed in a suitable container, heated to 80° C. under the protection of nitrogen, and stirred to dissolve; 12.0 g of egg yolk lecithin and 0.3 g of oleic acid were then weighed, and added thereto, and the mixture was stirred to dissolve to prepare an oil phase for use. Also 22.0 g of glycerol was weighed, and added to about 800 mL of water, and the mixture was heated to 80° C. under the protection of nitrogen, stirred to dissolve to prepare an aqueous phase. The above oil phase was added to the aqueous phase, and the mixture was sheared at a high speed of 19000 r/min for 10 minutes to disperse the oil phase in the aqueous phase, and additional water was added to a total volume of 1000 mL to prepare a primary emulsion. The primary emulsion was then homogenized 3 times by high-pressure homogenizer at 1000 bar pressure, so that the average particle size of the homogenized emulsion droplets was not more than 0.5 μm, filtered with a filter membrane, and the filtrate was filled in 2 mL, 5 mL, 10 mL glass ampoules under the protection of nitrogen, sterilized by rotary hot pressing at 121° C. for 8 min to obtain α-asarone emulsion injection, wherein the content of α-asarone was 10 mg/mL and the batch number was 20201228.

Preparation Embodiment 8 Preparation of α-Asarone Oral Emulsion 10.0 g of α-asarone and 100.0 g of pharmaceutically acceptable soybean oil were weighed, placed in a suitable container, heated to 80° C. under the protection of nitrogen, and stirred to dissolve; 12.0 g of egg yolk lecithin, 0.3 g of oleic acid, 10.0 g of antioxidant vitamin E and 2.0 g of ethylparaben were then weighed, and added thereto, and the mixture was stirred to dissolve to prepare an oil phase for use. Also 22.0 g of glycerol was weighed, and added to about 800 mL of water, and the mixture was heated to 80° C. under the protection of nitrogen, stirred to dissolve to prepare an aqueous phase. The above oil phase was added to the aqueous phase, and the mixture was sheared at a high speed of 19000 r/min for 10 minutes to disperse the oil phase in the aqueous phase, and additional water was added to a total volume of 1000 mL to prepare a primary emulsion. The primary emulsion was then homogenized 3 times by high-pressure homogenizer at 1000 bar pressure, so that the average particle size of the homogenized emulsion droplets was not more than 0.5 μm, filtered with a filter membrane, and the filtrate was filled in 10 mL oral penicillin bottle under the protection of nitrogen, sterilized by circulating steam at 100° C. for 30 min or sterilized by rotary hot pressing at 121° C. for 8 min to obtain α-asarone oral emulsion, wherein the content of α-asarone was 10 mg/mL and the batch number was 20210105.

Effect Embodiment 1: Short-Term Therapeutic Effect of α-Asarone on SAH and ICH Rats Experimental materials: SPF SD rats, half male and half female, weighing 200 to 240 g, were purchased from Sichuan Chengdu Dossy Experimental Animals Co., Ltd., with a certificate number as SCXK (Sichuan) 2020-030.

Collagenase VII was purchased from Sigma-Aldrich Company (specification: 1.5 KU; batch number: 000011586).

α-Asarone active pharmaceutical ingredient was purchased from Wuhan Lullaby Pharmaceutical Chemical Co., Ltd. (specification: 2 kg; batch number: 2883-98-9), and its emulsion injection was self-made, with batch numbers of 20201228, 20210105.

Vinpocetine injection was purchased from Henan Runhong Pharmaceutical Co., Ltd. (specification: 10 mg:2 mL; batch number: 1811283).

Nimodipine injection was purchased from Bayer Healthcare Company (specification: 10 mg:50 mL; batch number: BXJC71).

Experimental grouping: At 2 h after endovascular perforation or collagenase VII injection, Zea Longa score was used to evaluate the neurological function of rats. Successful model rats were randomly divided into groups for administration.

The rats were randomly divided into a sham group (group P, administrated the same volume of normal saline as the high-dose group of emulsion injection), a model group (group S or I, administrated the same volume of blank emulsion as the high-dose group of emulsion injection), low dose of α-asarone emulsion injection (prepared from preparation embodiment 7, 7.5 mg/kg, group L), medium dose of α-asarone emulsion injection (prepared from preparation embodiment 7, 15 mg/kg, group M), high dose of α-asarone emulsion injection (prepared from preparation embodiment 7, 30 mg/kg, group H), α-asarone emulsion oral administration group (prepared from preparation embodiment 8, 40 mg/kg, group O), β-asarone emulsion injection group (prepared into emulsion injection with a concentration of 10 mg/mL β-asarone by the same method as in preparation embodiment 7, 20 mg/kg, group B), vinpocetine injection group (commercially available, 2 mg/kg, group V), nimodipine injection group (commercially available, 1 mg/kg, group N), with 12 rats in each group. All groups were administrated through the tail vein injection except for group N administrated intraperitoneally.

1.1 Establishment of SAH by Endovascular Perforation

The rats were fasted for 12 hours before operation, and were anesthetized with 4% isoflurane, and kept anesthetized with 2% isoflurane. The animals were fixed in the supine position with the body temperature maintained at about 37° C. A traditional skin incision of the neck was performed along the midline. The muscle and fascia were separated along the medial margin of the sternocleidomastoid muscle to expose the right side, then the common carotid artery (CCA), external carotid artery (ECA) and internal carotid artery (ICA) were bluntly separated with disposal lines placed at CCA proximal end, ICA and ECA for use. The CCA proximal end and the ECA were ligated, and the ICA was temporarily clamped with an arterial clip, and then a small hole was poked with a needle at about 4 mm from the bifurcation at the CCA. A nylon suture was introduced into the CCA from the hole and advanced through the ICA after releasing the arterial clip, and the suture was inserted intracranially. When the suture was roughly 18 to 19 mm from the bifurcation of the common carotid artery, there was a sense of subtle resistance, indicating that the suture had reached the bifurcation of the anterior cerebral artery and the middle cerebral artery. The suture moved forward for roughly 2 mm to perforate the artery followed by instant withdraw, and then the suture was completely removed and the ICA was ligated. Finally, the incision was cleaned with normal saline and sutured. The sham group conducted the same procedure as the model group except for the perforation. After awakening from anesthesia, the animals were raised normally.

The SAH severity was grading after rat's euthanasia, i.e., completing the evaluation of short-term neurological function. The score was determined by the amount of subarachnoid hemorrhage on the surface of basal cistern and brain tissue which was divided into six parts by the Willis ring composed of basilar artery, anterior cerebral artery, internal carotid artery, posterior cerebral artery and posterior communicating artery. Each part was graded from 0 to 3 points according to the amount of subarachnoid blood clots, i.e., 0 points: no subarachnoid blood; 1 point: a small amount of subarachnoid blood; 2 points: moderate amount of blood clots with recognizable arteries; 3 points: blood clots cover all arteries in the area. All 6 part scores were added up for a total of 18 points. According to the final score, SAH hemorrhage severity could be divided into mild subarachnoid hemorrhage (0 to 7 points), moderate subarachnoid hemorrhage (8 to 12 points), and severe subarachnoid hemorrhage (13 to 18 points). The moderate to severe SAH models were selected for statistical analysis (score≥8 points).

1.2 Construction of ICH Model by Collagenase Injection

The rats were fasted for 12 hours before operation, and were anesthetized with 4% isoflurane, and kept anesthetized with 2% isoflurane. The animals were fixed in the prone position in a stereotaxic apparatus with the body temperature maintained at about 37° C. A traditional skin incision of the head was prepared along the midline. According to the stereotaxic atlas of the rat brain translated by Zhuge Qichao (George Paxinos, Charles Watson, Paxinos, Watson, & Zhuge Qichao. The Rat Brain in Stereotaxic Coordinates [M]. People's Medical Publishing House, 2005), the right caudate nucleus of the rat was determined as 0.0 mm anterior, 3.0 mm lateral to the bregma, and 5.5 mm ventral to the cortical surface. After labeling, we drilled an open window in the skull, and 1 μL of 0.5 U collagenase VII was slowly injected for 5 minutes with a microinjector. After the injection, the needle was stagnated for 8 minutes and slowly withdrawn. Then the scalp was sutured after the burr hole of skull was sealed with a sterile bone wax, and the rats were returned to the cage for normal feeding. The sham group conducted the same procedure as the model group, but received an equal volume of physiological saline into the caudate nucleus.

1.3 Enrollment Criteria of Cerebral Hemorrhage Model

According to Zea Longa's neurological function score, the rats were scored 2 hours after the operation when they were awake from anesthesia. Successful model rats with a score of 1 to 3 points were enrolled in the group:

0 points: no neurological deficits with normal activity;

1 point: inability to fully extend the contralateral forepaw;

2 points: the animal appears to turn in circles when crawling;

3 points: the animal tends to lean to the hemiplegic side;

4 points: the animal cannot walk spontaneously or loses consciousness.

1.4 Assessment of Short-Term Neurological Function

The neurological function of rats was comprehensively evaluated with Garcia score and beam balance test 24 hours after modeling. The criteria of Garcia score are shown in Table 1, which evaluates the movement, sensation, climbing and limb symmetry of the rats with the score range of 3 to 18 points. The lower the score, the more severe the neurological injury. The criteria of the beam balance test are shown in Table 2, which evaluated the proprioception and body coordination of rats with the score range of 0 to 6 points. The higher the score, the more severe the neurological injury. Scoring was done independently by a technician blinded to the modeling and drug administration.

TABLE 1

The criteria of Garcia score

| | Observation items | Score |
|---|---|---|
| Spontaneous movement (Putting rats in a cage and observing for 5 minutes) | No spontaneous movement | 0 points |
| | Very little movement | 1 point |
| | Moving and touching at least one side of the cage wall | 2 points |
| | Moving and touching at least three sides of the cage wall | 3 points |
| Symmetry of the body posture (Lifting the tail to suspend the rats and observing the state of the limbs) | No movement on the affected side | 0 points |
| | Slight movement of the affected side | 1 point |
| | Sluggish movement of the affected side | 2 points |
| | Bilateral body posture symmetry | 3 points |
| Forelimb extension (Suspending the tail to hang the hind limbs, making the rat walk only on the forelimbs on the table, and observing the forelimb movement) | No extension of the left forelimb | 0 points |
| | Slight extension of left forelimb | 1 point |
| | Left forelimb was extended but not as good as the right | 2 points |
| | Bilateral extensional symmetry | 3 points |
| Climbing experiment | Could not climb up | 1 point |
| | Left side disadvantage | 2 points |
| | Normal Climbing | 3 points |
| Bilateral body tactile reflex | No response on the left side | 1 point |
| | Left side was weaker than the right side | 2 points |
| | Same reactivity on both sides | 3 points |
| Bilateral beard tactile reflex | No response on the left side | 1 point |
| | Left side was weaker than the right side | 2 points |
| | Same reactivity on both sides | 3 points |

TABLE 2

The criterial of beam balance test

| Evaluation criteria | Score |
|---|---|
| Stable balance posture | 0 points |
| Grasping the edge of the balance beam | 1 point |
| Holding the balance beam tightly, and one limb dropped from the balance beam | 2 points |
| Holding the balance beam tightly, and two limbs dropped from the balance beam or rotated on the balance beam (>60 seconds) | 3 points |
| Trying to balance on a balance beam but falling (>40 seconds) | 4 points |
| Trying to balance on a balance beam but falling (>20 seconds) | 5 points |

TABLE 2-continued

The criterial of beam balance test

| Evaluation criteria | Score |
|---|---|
| Falling; no attempt to balance on a balance beam (<20 seconds) | 6 points |

As shown in Table 3, compared with the sham group (group P), the Garcia score of model group (group S or I) decreased significantly (P<0.001) and the beam balance score increased significantly (P<0.001) 24 hours after operation, implicating an obvious neurological impairment 24 hours after SAH or ICH. Intravenous administration of α-asarone at different doses (groups L, M, H) and oral administration of α-asarone (group O) could increase Garcia's score, reduce beam balance score, and thus ameliorating the neurological impairment induced by SAH or ICH to different degrees, wherein group M had the most significant effect (P<0.01). For SAH model, the curative effect of group M was better than that of nimodipine (group N, used to ameliorate vasospasm after subarachnoid hemorrhage) and vinpocetine (group V, used to treat the sequelae of cerebral hemorrhage). For ICH model, the curative effect in group L and M was better than that of group V, of which were significantly better than that of group N. On the contrary, β-asarone administration (group B) had no obvious effect against the neurological impairment in SAH and ICH model rats. In addition, the rat's brain was collected after the transcardinal perfusion. No significant difference was observed in the score of SAH severity between all SAH-induced groups, excluding the neurobehavioral difference induced by the modeling process.

TABLE 3

The score of short-term neurological function for rats

| | SAH model | | | | |
|---|---|---|---|---|---|
| | Neurological score | | | ICH model | |
| Group | Garcia score | Beam balance score | Bleeding score | Garcia score | Beam balance score |
| P | 16.08 ± 1.60 | 1.05 ± 0.89 | 0.25 ± 0.45 | 15.24 ± 0.86 | 1.55 ± 0.33 |
| S or I | 8.95 ± $1.93^{\#\#\#}$ | 4.63 ± $1.31^{\#\#\#}$ | 10.95 ± $2.33^{\#\#\#}$ | 8.87 ± $1.16^{\#\#\#}$ | 4.42 ± $1.12^{\#\#\#}$ |
| L | 10.82 ± $2.52^{\#\#\#}$ | 3.30 ± $1.85^{\#\#\#}$ | 10.94 ± $2.83^{\#\#\#}$ | 10.60 ± $1.28^{\#\#\#, *, \&}$ | 3.16 ± $1.22^{\#, *}$ |
| M | 12.29 ± $3.12^{\#\#, **}$ | 2.70 ± $1.21^{\#\#\#, **}$ | 10.64 ± $1.86^{\#\#\#}$ | 10.68 ± $1.05^{\#\#\#, *, \&}$ | 3.09 ± $0.94^{\#, **}$ |
| H | 11.79 ± $3.03^{\#\#\#, *}$ | 3.22 ± $1.21^{\#\#\#, *}$ | 11.75 ± $2.01^{\#\#\#}$ | 10.01 ± $1.24^{\#\#\#}$ | 3.31 ± $1.31^{\#\#,}$ |
| O | 10.94 ± $2.02^{\#\#\#}$ | 3.30 ± $2.07^{\#\#\#}$ | 10.39 ± $1.98^{\#\#\#}$ | 10.17 ± $1.23^{\#\#\#}$ | 3.41 ± $1.25^{\#\#}$ |
| N | 11.33 ± $2.42^{\#\#\#, *}$ | 3.01 ± $1.53^{\#\#\#, *}$ | 10.78 ± $2.86^{\#\#\#}$ | 8.92 ± $1.72^{\#\#\#}$ | 3.89 ± $1.21^{\#\#\#}$ |
| V | 10.30 ± $3.15^{\#\#\#}$ | 3.54 ± $1.33^{\#\#\#}$ | 11.40 ± $2.10^{\#\#\#}$ | 10.56 ± $1.01^{\#\#\#, *, \&}$ | 3.27 ± $0.97^{\#\#, *}$ |
| B | 10.51 ± $2.21^{\#\#\#}$ | 3.70 ± $1.75^{\#\#\#}$ | 11.20 ± $1.92^{\#\#\#}$ | 9.12 ± $1.34^{\#\#\#}$ | 3.76 ± $0.87^{\#\#\#}$ |

Note:
$^{\#\#\#}P < 0.001$,
$^{\#\#}P < 0.01$,
$^{\#}P < 0.05$ vs. the sham group (group P),
$^{**}P < 0.01$,
$^{*}P < 0.05$ vs. the model group (group S or I),
$^{\&}P < 0.05$ vs. nimodipine group (group N).
The data were expressed as x ± SD and analyzed by ANOVA followed by Tukey-post-hoc for comparative analyses of multiple groups.

Effect Embodiment 2: α-Asarone Reduced the Incidence of Secondary Epilepsy in SAH Rats The experimental materials, grouping, modeling method and administration protocol were the same as those in the effect embodiment 1, and the seizures of rats in each group were observed within 24 hours after SAH. As shown in Table 4, compared with group P, the Racine score of group S was significantly increased ($P<0.001$), which was reduced to different degrees in group L, M, H and O, wherein group M demonstrated most significant reduction ($P<0.05$). Therefore, α-asarone could significantly reduce the incidence of secondary epilepsy in SAH rats.

TABLE 4

Effect of α-asarone on secondary epilepsy in SAH rats

| Group | Racine score | Clonic seizures (%) | Tonic seizures (%) |
|---|---|---|---|
| P | 0 ± 0 | 0 | 0 |
| S | $1.72 \pm 1.87^{\#\#\#}$ | 38.9% | 11.1% |
| L | 0.53 ± 1.46 | 6.7% | 6.7% |
| M | $0.44 \pm 1.34^{*}$ | 5.6% | 5.6% |
| H | $0.73 \pm 1.44^{\#}$ | 8.0% | 6.7% |
| O | $0.77 \pm 1.59^{\#}$ | 15.4% | 7.7% |
| N | $0.81 \pm 1.56^{\#}$ | 18.8% | 6.2% |

Note:
$^{\#\#\#}P < 0.001$,
$^{\#}P < 0.05$ vs. group P (administration of normal saline), and
$^{*}P < 0.05$ vs. group S (administration of blank emulsion). The seizure grade was divided into 6 grades based on the Racine's scale according to the degree of seizure: grade 0 was no response or convulsion cessation, grade I was rhythmic twitching of mouth or facial, grade II was head nodding or tail flicking, grade III was single limb twitching, grade IV was multi-limb twitching or tonic seizure, and grade V was full tonic-clonic seizures. Grades I, II and III were clonic seizures, while grades IV and V were tonic seizures.

Effect Embodiment 3: Long-Term Protective Effect of α-Asarone on SAH Rats

3.1 Long-Term Survival Rate of SAH Rats

The experimental materials, grouping and modeling methods were the same as those in effect embodiment 1. The rats were immediately administrated 2 hours after SAH modeling according to the grouping administration protocol and continued to be administrated once a day for 14 days thereafter, and the survival of the rats was observed and recorded for 14 days. The results are shown in Table 5. The mortality rate within 24 hours in group S was as high as 53.8%. On the contrary, the administration in group M, H, O and N significantly reduced the mortality rate within 24 hours and prolonged the survival time of SAH rats, i.e., α-asarone could significantly reduce the mortality rate within 24 hours and prolong the survival time of 14 days in SAH rats.

TABLE 5

Long-term survival rate of SAH rats

| Group | Day 0 (Number of rats) | Day 14 (Number of rats) | 24-hour mortality rate | Survival rate |
|---|---|---|---|---|
| P | 6 | 6 | 0 | 100.0% |
| S | 26 | 9 | 53.8% | 34.6% |
| L | 8 | 3 | 50.0% | 37.5% |
| M | 13 | 8 | 23.1% | 61.5% |
| H | 9 | 5 | 22.2% | 55.6% |
| O | 8 | 5 | 25.0% | 62.5% |
| N | 12 | 7 | 25.0% | 58.3% |

3.2 Evaluation of Long-Term Learning and Memory Function

Morris water maze was used to evaluate the long-term spatial perception and memory ability of rats in each group, and was performed after the survival observation, i.e., 15 to 19 days after SAH. The water maze was a circular pool with a diameter of 150 cm and a depth of 60 cm. Before the experiment, warm water (24±2)° C. was filled to a depth of 30 cm and colored black with ink. The pool was equally divided into four quadrants, and different signs were pasted on the walls of different quadrants to indicate the difference. A transparent platform with a diameter of 10 cm and a height of 28 cm was placed in the center of one quadrant, and was 2 cm beneath the water. Rats were released from the designated quadrant according to the experimental guidelines. On day 1 to 4, rats were successively released into water from four corresponding quadrants with a 10-minute interval. If the rat found the platform within 60 seconds, it was allowed to remain there for 10 seconds; if not, it was guided to the platform with a rod and allowed to stand there for 10 seconds. On day 5, the platform was removed and the rats were allowed to swim freely for 60 seconds. The escape latency, swimming speed and dwelling time on the target quadrant were recorded using a computerized tracking system (Noldus Ethovision, Tacoma, WA, USA).

Figure 1B:
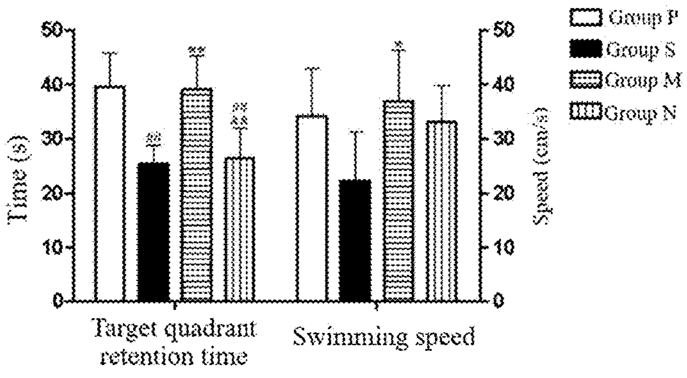
Figure 1C:
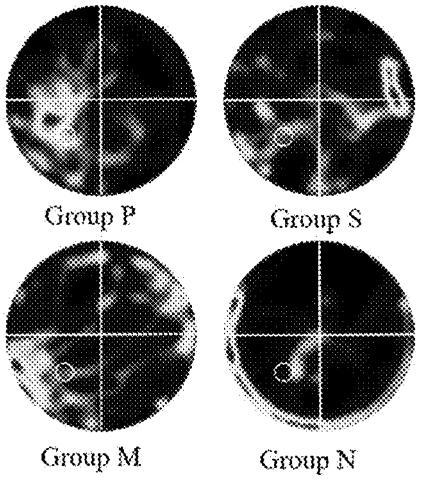
Figure 1D:
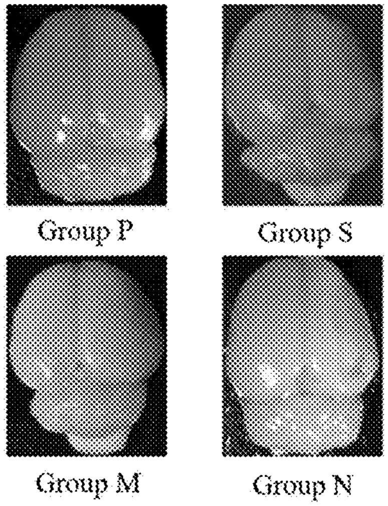
Figure 2A:
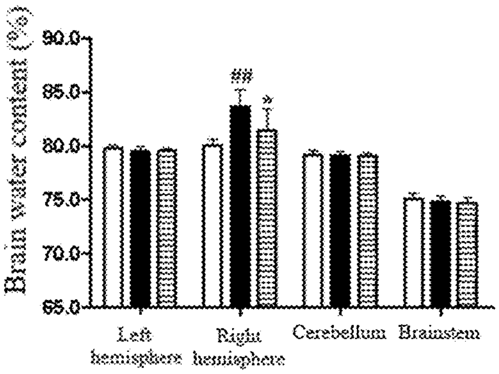
FIGS. 2A-2D. Effects of α-asarone on brain edema and blood-brain barrier permeability in model rats.
Figure 2B:
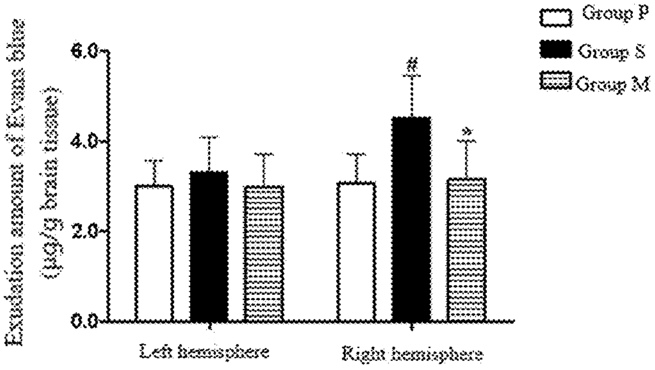
Figure 2C:
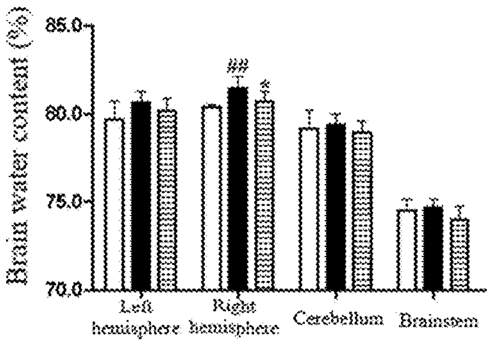
Figure 2D:
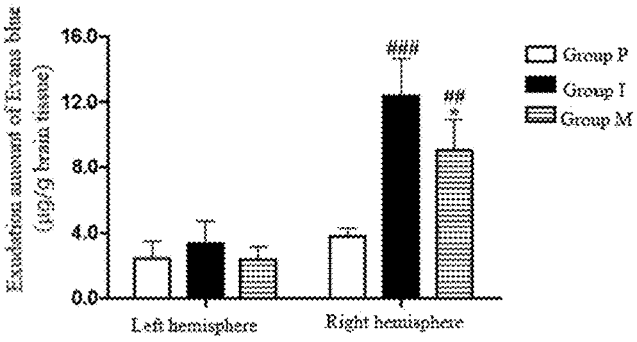
Figure 3A:
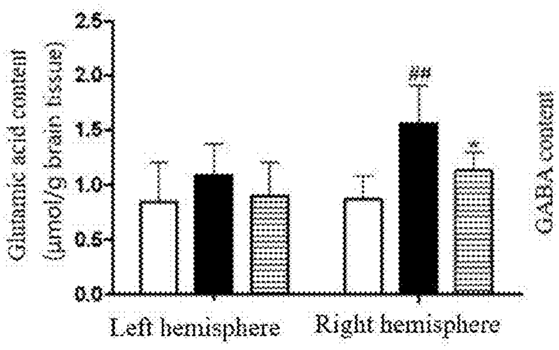
FIGS. 3A-3D. Effect of α-asarone on the content of glutamate and GABA in brain tissue of model rats.
Figure 3B:
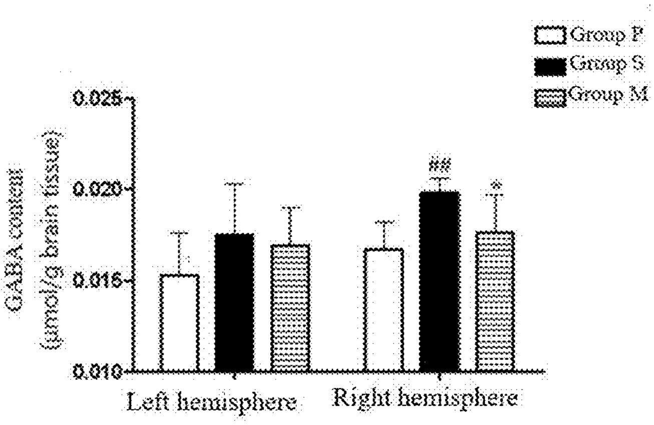
Figure 3C:
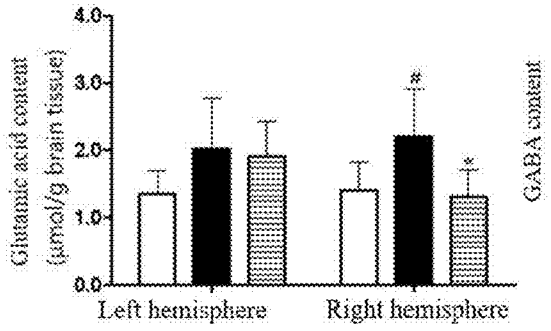
Figure 3D:
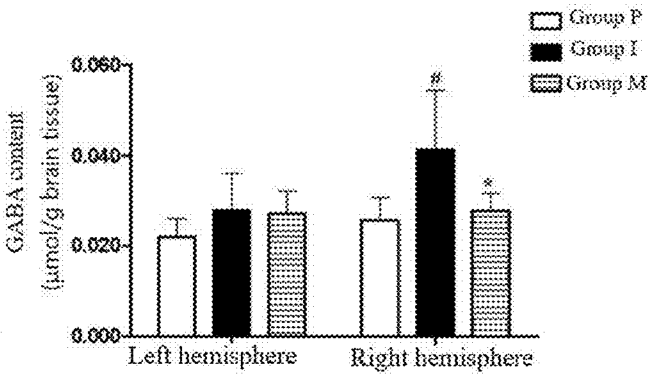
Figure 4A:
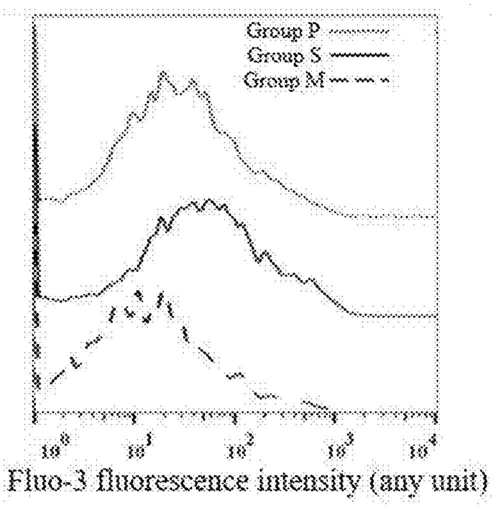
FIGS. 4A-4F. Effects of α-asarone on calcium level and mitochondrial membrane potential in brain tissue of model rats.
Figure 4B:
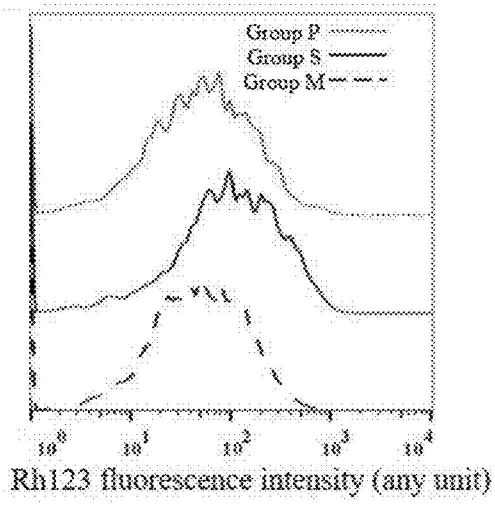
Figure 4C:
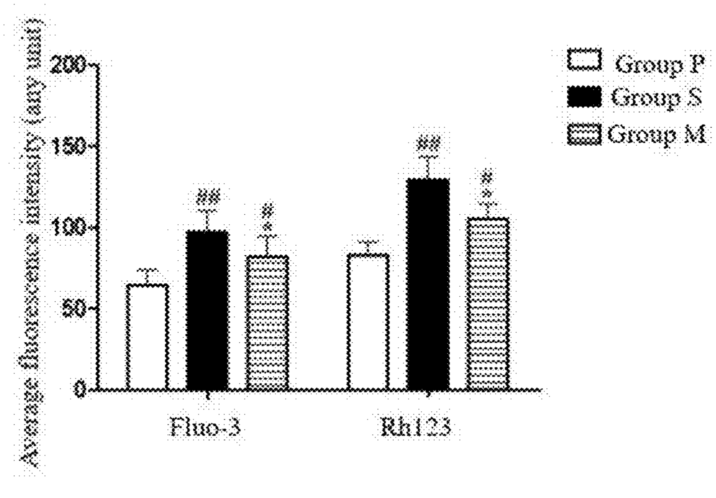
Figure 4D:
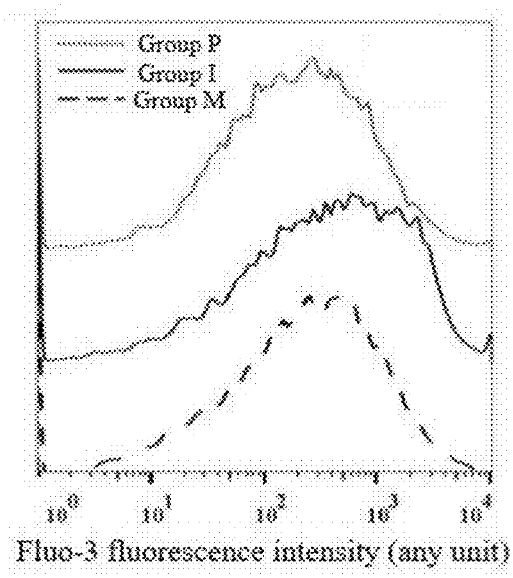
Figure 4E:
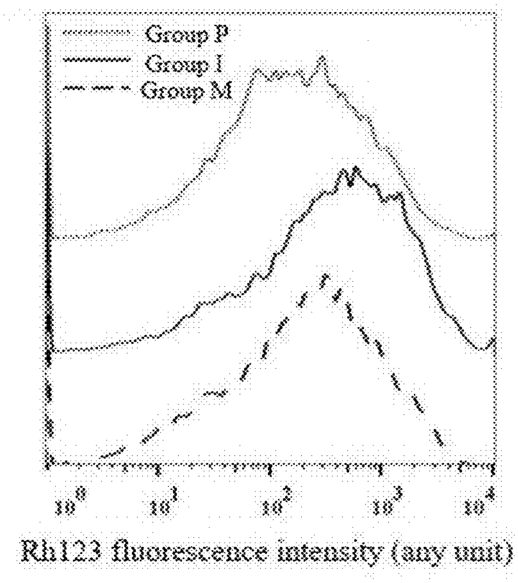
Figure 4F:
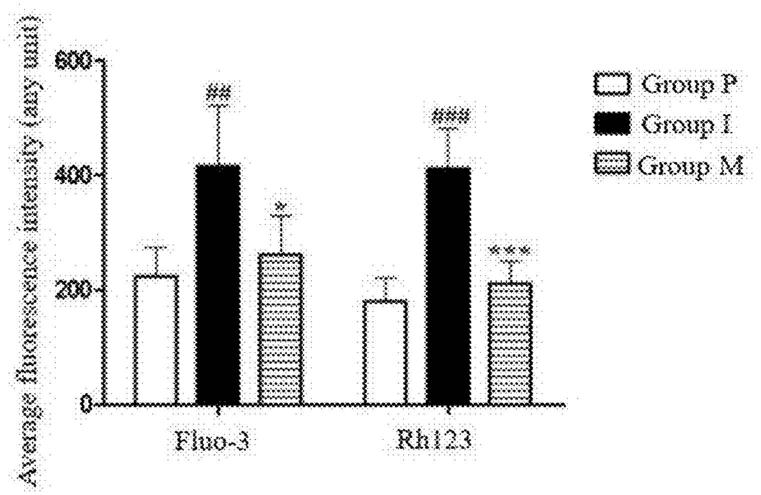

The experimental results are shown in FIG. 1A, during the training period, the escape latency for rats was significantly longer in group S and N compared with group P ($P<0.001$), which was significantly decreased in group M and was not even statistically different from group P by day 4. As shown in FIGS. 1B and 1C, during spatial probe test, compared with group P, rats in group S and N spent significantly less time in the target quadrant, which was notably prolonged in group M and comparable to that of group P. In addition, the swimming speed of group M was significantly faster than that of group S ($P<0.05$). As shown in FIG. 1D, the rat's brain in group S and N was notably atrophied, which was significantly rescued in group P and M after long-term administration. In conclusion, long-term administration of α-asarone could not only significantly improve the learning and memory function and promote the recovery of motor function in SAH rats, but also alleviate the atrophy of brain tissue in SAH rats during recovery phase.

Effect Embodiment 4: Study on the Mechanism of Action of α-Asarone Against Hemorrhagic Stroke Experimental Materials:

- Evans Blue (C11891158, Shanghai Macklin Biochemical Technology);
- formamide (20190716, Tianjin Bodi Chemicals);
- glutamate detection kit (20210525, Beijing Solarbio Technology);
- GABA-Elisa kit (202101, Shanghai Jianglai Biology);
- DNAase I (226F031, Beijing Solarbio Technology);
- papain (111S022, Beijing Solarbio Technology);
- calcium ion fluorescent probe (20210313, Jiangsu Keygen Biology);

rhodamine 123 dye solution (1191033, Beijing Solarbio Technology);

ice-cold centrifugal buffer (20210525, Beijing Solarbio Technology).

Experimental Steps and Results:

4.1 Measurement of Brain Water Content and Blood-Brain Barrier Permeability

After completing the evaluation of 24-hour short-term neurological function, 4% Evans blue solution (2.5 mL/kg) was injected into the right caudal vein of the rats. After circulated for 1 hour, the rats were deeply anesthetized and transcardinally perfused with 100 mL of normal saline to collect the rats' brain. The whole brain was divided into four groups: left hemisphere (LH), right hemisphere (RH), cerebellum (Cb) and brainstem (BS). The left and right hemispheres were coronally divided into two parts, one part was immediately weighed (wet weight) with a balance with an accuracy of 0.1 mg, dried in an oven at 105° C. for 24 hours and weighed again (dry weight). The brain water content was calculated as [(wet weight−dry weight)/wet weight]×100%. The other part of the brain tissue was weighed (wet weight) and emerged into 10 times the volume of pure formamide, incubated at 60° C. for 48 hours, centrifuged at 25° C. for 30 min (10,000 rpm/min). The Evans blue in the supernatant was measured at 622 nm by a UV spectrophotometry, and calculated with a standard curve for quantification. The amount of Evans blue was expressed as μg/g of brain tissue (wet weight).

As shown in FIGS. 2A-2D, compared with the sham group (group P), the brain water content and the Evans blue extravasation of the hemorrhagic hemisphere and the impairment of blood-brain barrier in the model group (group S or I) was significantly increased 24 hours after operation. However, intravenous administration of α-asarone at medium-dose (group M) could significantly reduce the brain water content and Evans blue content, thus alleviating the brain edema, Evans blue extravasation and blood-brain barrier impairment.

4.2 Determination of Glutamate and GABA Content

The rats were deeply anesthetized, and decapitated to collect the brain at 12-24 hours after modeling. Then about 60 to 120 mg of brain cortex on the hemorrhagic side were weighed, homogenized with 10 times the volume of ice-cold centrifuge buffer for biochemical detection, homogenized for 10 min in an ice bath, and centrifuged at 4° C. for 30 minutes (14,000 rpm/min). The contents of glutamate and GABA in the supernatant were detected according to the instructions of glutamate content detection kit and rat GABA Elisa kit.

The results are shown in FIGS. 3A-3D. Compared with group P, the contents of glutamate and GABA in the hemorrhagic hemisphere in the group S or I were significantly higher 12 to 24 hours after operation, while the administration in group M could significantly reduce the contents of glutamate and GABA in the hemorrhagic brain tissue of rats, which was beneficial to counteract glutamate-involved excitotoxicity, restore the excitatory amino acid/inhibitory amino acid (EAA/IAA) balance in the brain, and improve the motor function of rats.

4.3 Determination of $Ca^{2+}$ Level or Mitochondrial Membrane Potential

The rats were decapitated to collect the brain 12 to 24 hours after modeling. The brain cortex around the hematoma was immediately taken to prepare a single cell suspension by enzymatic digestion (papain: 2 mg/mL; DNAase I: 0.05 mg/mL), with the cell concentration was adjusted to $5\times10^6$ cells/mL. 100 μL of cell suspension was incubated with 5 μM Fluo-3/AM dye solution or 10 μM Rhodamine 123 dye solution at 37° C. for 45 min. Then the cells were washed twice with PBS (phosphate buffer, pH=7.2-7.4), resuspended with 0.5 mL of PBS, and detected by a flow cytometry at the excitation wavelength of 506 nm and the emission wavelength of 526 nm. The mean fluorescence intensity of Fluo-3 and Rh123 in 10,000 cells was analyzed by FlowJo software.

The results are shown in FIGS. 4A-4F. Compared with group P, group S or I showed significantly higher calcium level and mitochondrial membrane potential 12-24 hours after operation, suggesting the destruction of mitochondria and increase of apoptosis. However, administration in group M could significantly reduce calcium level and stabilize mitochondrial membrane potential, thus reducing neuronal apoptosis and necrosis.

Effect Embodiment 5: Protective Effect of α-Asarone on Oxyhemoglobin-Damaged Neurons Experimental Materials:

PC12 cell line was purchased from Wuhan Procell Life Science & Technology Co., Ltd.;

oxyhemoglobin (20210201, Beijing Solarbio Technology Co., Ltd.);

MTT (C12029690, Sigma-Aldrich, USA);

DMEM high-glucose culture medium (AG29301810, Hyclone, USA);

fetal bovine serum (20010401, Gibco, USA);

penicillin-streptomycin solution (dual antibiotics) (20201220, Hyclone Company, USA);

PBS powder (WK173618-1, Beijing Zhongshan Goldenbridge Biotechnology Co., Ltd.);

DMSO (20201220, Beijing Solarbio Technology Co., Ltd.).

Experimental Steps:

Complete culture medium: DMEM high-glucose culture medium, fetal bovine serum and penicillin-streptomycin solution (dual antibiotics) were mixed at a volume ratio of 90:9:1 and stored at 4° C. in the refrigerator.

Serum-free culture medium: DMEM high-glucose culture medium and penicillin-streptomycin solution (dual antibiotics) were mixed at a volume ratio of 99:1 and stored at 4° C. in the refrigerator.

PC12 cells in the logarithmic phase of growth were seeded in a 96-well plate ($1\times10^4$ cells/100 μL/well) with the marginal wells filled with sterile PBS, and cultured with complete culture medium at 37° C. with 5% $CO_2$ for 24 hours until the cells completely adhered to the wall. The supernatant was discarded followed by oxyhemoglobin incubation at 37° C. with 5% $CO_2$ for 24 hours with final concentrations of 0 μM, 4 μM, 6 μM, 8 μM and 10 μM, respectively. Subsequently, 10 μL MTT (5 mg/mL) was added into each well and incubated at 37° C. with 5% $CO_2$ for 4 hours. Then, the supernatant was discarded, the formazan was dissolved with 100 μL DMSO, and the optical density (OD) was gauged at 570 nm by a microplate reader after incubation at 37° C. for 15 minutes (500 r/min) to calculate the cell viability. According to the formula "fold of cell abnormal proliferation=[(average absorbance value of the experimental group−average absorbance value of zero-adjusting well)/(average absorbance value of the control group−average absorbance value of zero-adjusting well)", 6 μM oxyhemoglobin was screened out for following in vitro pharmacodynamic experiment since it produced a maximum of 1.5-fold abnormal cell proliferation compared to the control group. Accordingly, this concentration was used as the optimal concentration of oxidative stress injury model induced by oxyhemoglobin in pre-test for the following cell pharmacodynamic experiments.

Figure 5:
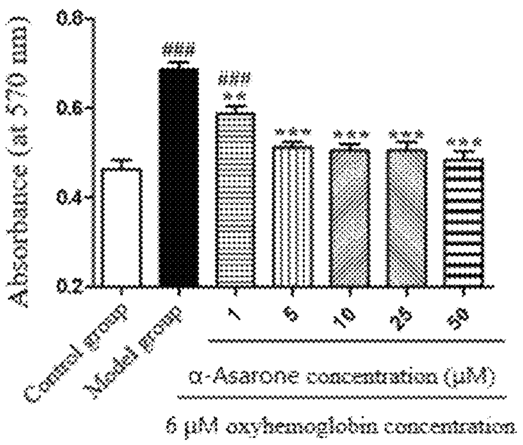
FIG. 5. Effects of different doses of α-asarone on PC12 cells injured by 6 μM oxyhemoglobin. ###P<0.001, ##P<0.01 vs. the control group, *P<0.001, P<0.01 vs. the model group.

PC12 cells in the logarithmic phase of growth were seeded in a 96-well plate ($1\times10^4$ cells/100 μL/well) with the marginal wells filled with sterile PBS, and cultured with complete culture medium at 37° C. with 5% $CO_2$ for 24 hours until the cells completely adhered to the wall. The supernatant was discarded, and the cells were pre-incubated with different doses of 100 μL of α-asarone emulsion (prepared in preparation embodiment 7, the final concentrations of α-asarone were 1 μM, 5 μM, 10 μM, 25 μM, 50 μM, respectively) diluted by serum-free culture medium except the control group and the model group. After incubation for 2 hours, oxyhemoglobin solution at a final concentration of 6 μM diluted with serum-free medium was added to the above administration groups, 20 μL per well, and continued to incubate at 37° C. with 5% $CO_2$ for 24 hours. In the control group, only the same volume of serum-free medium was added; in the model group, 100 μL of blank emulsion diluted with serum-free medium (the prescription was the same as the preparation embodiment 7 except that it did not contain α-asarone) and 20 μL of oxyhemoglobin solution diluted with serum-free medium at a final concentration of 6 μM were added sequentially; the rest of the operations in the control and model groups were the same as those in the administration group. Then, 10 μL MTT (5 mg/mL) was added into each well and incubated at 37° C. with 5% $CO_2$ for 4 hours. The supernatant was discarded, the formazan was dissolved with 100 μL DMSO, and the optical density (OD) was gauged at 570 nm by a microplate reader after incubation at 37° C. for 15 minutes (500 r/min) to calculate the cell viability. The results are shown in FIG. 5.

Experimental results: As shown in FIG. 5, compared with the control group, the absorbance of PC12 cells in the model group increased significantly, suggesting that the cells proliferated abnormally accompanied by obvious oxidative stress after oxyhemoglobin incubation. However, different concentrations of α-asarone significantly reduced the abnormal increase of cell vitality caused by oxyhemoglobin, indicating that α-asarone could significantly reduce the oxidative stress reaction caused by oxyhemoglobin (FIG. 5).

Effect Embodiment 6: Preliminary Evaluation of the Safety of α-Asarone Emulsion Injection-Mouse Bone Marrow Micronucleus Test Experimental materials: 50 SPF male Kunming mice, weighing 18 to 22 g, were purchased from Chengdu Dossy Experimental Animals Co., Ltd., with a license number as SCXK (Sichuan) 2020-030. Cyclophosphamide for injection was purchased from Jiangsu Shengdi Pharmaceutical Co., Ltd. 1,4-piperazinediethanesulfonic acid (PIPES, 715H021), TritonX-100 (829I0210), and propidium iodide (PI, 1024S043) were bought from Beijing Solarbio Company.

Experimental grouping and administration: The animals were randomly divided into five groups with 10 rats in each group: blank control group (blank group, administrated blank emulsion with the same volume as the high-dose group of α-asarone), cyclophosphamide group (CTX group, 40 mg/kg), low dose of α-asarone emulsion injection group (prepared by preparation embodiment 7, 100 mg/kg/day, ASA-L group), medium dose of α-asarone emulsion injection group (prepared by preparation embodiment 7, 150 mg/kg/day, ASA-M group), and high dose of α-asarone emulsion injection group (prepared from preparation embodiment 7, 200 mg/kg/day, ASA-H group).

All drugs were administrated through the tail vein for continuous 4 days except for the single injection of the positive control drug cyclophosphamide (CTX) 24 hours before sampling. After 24 hours of the last administration, the mice were sacrificed to separate both femurs. The femoral bone marrow cells were washed with PBS and filtered by 300 mesh nylon cell sieves to prepare a single-cell suspension. The suspension was centrifuged at 1650 rpm for 5 min, and the cell concentration was adjusted to $5\times10^6$ cells/mL by PBS resuspension. For each sample, 100 μL of the cell suspension was incubated with 400 μL of the PIPES-PI solution (10 mL of PIPES solution (concentration of 3.5 mg/mL)+0.5 mg PI+0.01 mL Triton X-100 (concentration of 0.1%)), gently blown and mixed, at 4° C. in the dark for 30 min and detected by a flow cytometry. The results are shown in Table 6. As shown in Table 6, PCE indicated polychromatic erythrocytes, MNPCE indicated polychromatic erythrocytes containing micronucleus, and fMNPCE indicated the ratio of polychromatic erythrocytes containing micronucleus to polychromatic erythrocytes, reflecting the micronucleus rate of mouse bone marrow cells. The higher the value, the stronger the genotoxicity.

The results are shown in Table 6, the micronucleus rate of the positive control drug cyclophosphamide group (CTX) was significantly higher than that of the blank emulsion group ($P<0.01$). However, there was no significant difference in micronucleus rate between different doses of α-asarone emulsion injection compare to the blank emulsion group, while a significant decreasing micronucleus rate was observed compare with the CTX group (ASA-L: $P<0.01$; ASA-M: $P<0.05$; ASA-H: $P<0.05$).

The above in vivo toxicological studies of chromosome damage in the hematopoietic cells of mice showed that no significant changes were observed in the micronucleus rate of mouse bone marrow cells in mice at an intravenous dose of up to 200 mg/kg for α-asarone emulsion injection. Considering its aforementioned effective dosage for the treatment of hemorrhagic stroke, the safety profile of the drug was expected to be good.

TABLE 6

Results of bone marrow fMNPCE (‰) detected by flow cytometry in mice

| Group | PCE | MNPCE | fMNPCE (‰) |
|---|---|---|---|
| Blank group | 47.03 ± 7.03 | 0.36 ± 0.08 | 7.54 ± 0.59 |
| CTX group | 36.46 ± 8.01 | 0.86 ± 0.25 | 24.36 ± 8.03$^{##}$ |
| ASA-L group | 40.58 ± 9.17 | 0.39 ± 0.11 | 10.10 ± 2.75$^{**}$ |
| ASA-M group | 38.37 ± 3.18 | 0.47 ± 0.19 | 12.34 ± 5.52$^{*}$ |
| ASA-H group | 41.39 ± 6.11 | 0.55 ± 0.43 | 12.60 ± 8.53$^{*}$ |

Note:
$^{##}P < 0.01$ vs. blank group,
$^{**}P < 0.01$,
$^{*}P < 0.05$ vs. CTX group.

In summary, the results of in vitro and in vivo pharmacodynamic studies showed that α-asarone could significantly improve the short-term neurobehavioral function and long-term learning and memory function of rats with hemorrhagic stroke, reduce the mortality and incidence of secondary epilepsy in SAH rats, alleviate brain edema and blood-brain barrier impairment, and prevent or relieve brain tissue atrophy in the recovery period. Further mechanism research indicated that α-asarone antagonized glutamate-involved excitotoxicity, reduced GABA level and thus restoring EAA/IAA balance in the brain, inhibited $Ca^{2+}$ influx, stabilized mitochondrial membrane potential, and thereby reducing neuronal apoptosis, relieving oxidative stress and exerting neuroprotective effect. Therefore, α-asarone is expected to be a promising drug for treating hemorrhagic stroke.

Although the specific embodiments of the present disclosure have been described above, those skilled in the art should understand that these are only examples, and many changes or modifications can be made to these embodiments without departing from the principle and essence of the present disclosure. Therefore, the scope of protection of the present disclosure is defined by the appended claims.

The invention claimed is:

1. A method for treating hemorrhagic stroke in a subject, comprising:

administrating to the subject a therapeutically effective amount of a compound represented by formula I;

(I)

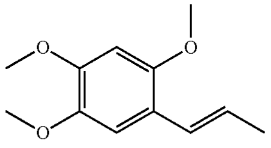

wherein, the compound represented by formula I is the only active ingredient in the method; the hemorrhagic stroke is a stroke caused by at least one of intracerebral hemorrhage and subarachnoid hemorrhage.

2. The method as claimed in claim 1, wherein, the method is used for treating hemorrhagic stroke and secondary epilepsy caused by hemorrhagic stroke.

3. The method as claimed in claim 1, wherein, the method is used for at least one of the following: alleviating neurological or motor dysfunction caused by ICH or SAH, reducing brain edema or blood-brain barrier dysfunction in acute phase caused by ICH or SAH, reducing the mortality in acute phase caused by hemorrhagic stroke, prolonging survival time, ameliorating long-term learning and memory dysfunction caused by hemorrhagic stroke, and preventing or alleviating brain tissue atrophy during recovery phase of hemorrhagic stroke.

4. The method as claimed in claim 1, wherein, the method further comprises administrating to the subject pharmaceutical excipients.

5. The method as claimed in claim 1, wherein, when the method is used for treating a human suffering from hemorrhagic stroke, the daily administration dosage range of the compound represented by formula I is 0.15 mg to 5.0 mg/kg body weight.

6. The method as claimed in claim 1, wherein, the administration route is injection or oral administration.

7. The method as claimed in claim 1, wherein, the compound represented by formula I is administrated in a form of emulsion.

8. A method for treating hemorrhagic stroke in a subject, comprising: administrating to the subject a pharmaceutical composition, wherein the pharmaceutical composition comprises a compound represented by formula I and pharmaceutical excipients;

(I)

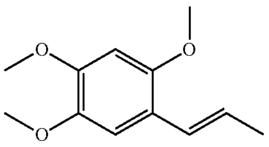

wherein, the compound represented by formula I is the only active ingredient in the pharmaceutical composition; the hemorrhagic stroke is a stroke caused by at least one of intracerebral hemorrhage and subarachnoid hemorrhage.

9. The method as claimed in claim 8, wherein, the method is used for treating hemorrhagic stroke and secondary epilepsy caused by hemorrhagic stroke.

10. The method as claimed in claim 4, wherein, the total weight ratio of the compound represented by formula I to the pharmaceutical excipients is 1:20 to 1000.

11. The method as claimed in claim 5, wherein, the daily administration dosage range of the compound represented by formula I is 0.3 mg to 3.0 mg/kg body weight.

12. The method as claimed in claim 1, wherein, the hemorrhagic stroke is a stroke caused by intracerebral hemorrhage.

13. The method as claimed in claim 1, wherein, the hemorrhagic stroke is a stroke caused by subarachnoid hemorrhage.

14. The method as claimed in claim 8, wherein, the hemorrhagic stroke is a stroke caused by intracerebral hemorrhage.

15. The method as claimed in claim 8, wherein, wherein, the hemorrhagic stroke is a stroke caused by subarachnoid hemorrhage.

* * * * *